United States Patent [19]

Berg

[11] Patent Number: 5,407,540
[45] Date of Patent: Apr. 18, 1995

[54] SEPARATION OF 3-METHYL-2-BUTANOL FROM 1-BUTANOL BY EXTRACTIVE DISTILLATION

[75] Inventor: Lloyd Berg, 1314 S. Third Ave., Bozeman, Mont. 59715

[73] Assignee: Lloyd Berg, Bozeman, Mont.

[21] Appl. No.: 311,267

[22] Filed: Sep. 23, 1994

[51] Int. Cl.6 .......................... B01D 3/40; C07C 29/84
[52] U.S. Cl. .......................................... 203/57; 203/58; 203/59; 203/60; 203/63; 203/62; 203/65; 203/68; 203/69; 568/913
[58] Field of Search ....................... 203/60, 69, 62, 68, 203/63, 58, 57, 59, 65; 568/913, 918

[56] References Cited

U.S. PATENT DOCUMENTS

| 2,552,911 | 5/1951 | Steitz | 203/69 |
| 2,575,243 | 11/1951 | Carlson et al. | 203/60 |
| 2,583,412 | 1/1952 | Carlson et al. | 203/65 |
| 4,756,803 | 7/1988 | Berg | 203/60 |
| 5,360,520 | 11/1994 | Berg | 203/60 |

*Primary Examiner*—Wilbur Bascomb, Jr.

[57] ABSTRACT

3-Methyl-2-butanol is difficult to separate from 1-butanol by conventional distillation or rectification because of the proximity of their boiling points. 3-Methyl-2-butanol can be readily separated from 1-butanol by extractive distillation. Effective agents are ethyl n-valerate, dimethylacetamide and dimethylsulfoxide.

1 Claim, No Drawings

SEPARATION OF 3-METHYL-2-BUTANOL FROM 1-BUTANOL BY EXTRACTIVE DISTILLATION

FIELD OF THE INVENTION

This invention relates to a method for separating 3-methyl-2-butanol from 1-butanol using certain organic liquids as the agent in extractive distillation.

DESCRIPTION OF PRIOR ART

Extractive distillation is the method of separating close boiling compounds from each other by carrying out the distillation in a multiplate rectification column in the presence of an added liquid or liquid mixture, said liquid(s) having a boiling point higher than the compounds being separated. The extractive agent is introduced near the top of the column and flows downward until it reaches the stillpot or reboiler. Its presence on each plate of the rectification column alters the relative volatility of the close boiling compounds in a direction to make the separation on each plate greater and thus require either fewer plates to effect the same separation or make possible a greater degree of separation with the same number of plates. The extractive agent should boil higher than any of the close boiling liquids being separated and not form minimum azeotropes with them. Usually the extractive agent is introduced a few plates from the top of the column to insure that none of the extractive agent is carried over With the lowest boiling component. This usually requires that the extractive agent boil about twenty Celcius degrees or more higher than the highest boiling component.

At the bottom of a continuous column, the less volatile components of the close boiling mixtures and the extractive agent are continuously removed from the column. The usual methods of separation of these two components are the use of another rectification column, cooling and phase separation, or solvent extraction.

The usual method of evaluating the effectiveness of extractive distillation agents is the change in relative volatility of the compounds to be separated. Table 1 shows the degree of separation or purity obtainable by theoretical plates at several relative volatilities. Table 1 shows that a relative volatility of at least 1.2 is required to get an effective separation by rectification.

TABLE 1

Effect of Relative Volatility on Theoretical Stage Requirements.

| Separation Purity, Both Products (Mole Fraction) | Relative Volatility | | | | | | | |
|---|---|---|---|---|---|---|---|---|
| | 1.02 | 1.1 | 1.2 | 1.3 | 1.4 | 1.5 | 2.0 | 3.0 |
| | Theoretical Stages at Total Reflux | | | | | | | |
| 0.999 | 697 | 144 | 75 | 52 | 40 | 33 | 19 | 12 |
| 0.995 | 534 | 110 | 57 | 39 | 30 | 25 | 14 | 9 |
| 0.990 | 463 | 95 | 49 | 34 | 26 | 22 | 12 | 7 |
| 0.98 | 392 | 81 | 42 | 29 | 22 | 18 | 10 | 6 |
| 0.95 | 296 | 61 | 31 | 21 | 16 | 14 | 8 | 4 |
| 0.90 | 221 | 45 | 23 | 16 | 12 | 10 | 5 | 3 |

There are a number of commercial processes which produce complex mixtures of alcohols, e.g. the Fischer-Tropsch process which produces a series of homologous alcohols. Two of the commonest alcohols usually present are 3-methyl-2-butanol, B.P.=112° C. and 1-butanol, B.P.=118° C. The relative volatility between these two is 1.22 which makes it very difficult to separate them by conventional rectification. Extractive distillation would be an attractive method of effecting the separation of 3-methyl-2-butanol from 1-butanol if agents can be found that (1) will create a large apparent relative volatility between 3-methyl-2-butanol and 1-butanol and (2) are easy to recover from the 1-butanol. Table 2 shows the relative volatility required to obtain 99% purity. With no agent, the relative volatility is 1.22 and 63 actual plates as required. With an agent giving a relative volatility of 1.8, only 22 plates are required.

TABLE 2

Theoretical And Actual Plates Required vs. Relative Volatility For 3-Methyl-2-butanol - 1-Butanol Separation

| Relative Volatility | Theoretical Plates Required At Total Reflux, 99% Purity | Actual Plates Required 75% Efficiency |
|---|---|---|
| 1.22 | 47 | 63 |
| 1.3 | 35 | 47 |
| 1.4 | 27 | 36 |
| 1.7 | 18 | 24 |
| 1.8 | 16 | 22 |

OBJECTIVE OF THE INVENTION

The object of this invention is to provide a process or method of extractive distillation that will enhance the relative volatility of 3-methyl-2-butanol from 1-butanol in their separation in a rectification column. It is a further object of this invention to identify organic compounds which in addition to the above constraints, are stable, can be separated from 1-butanol and recycled to the extractive column with little decomposition.

SUMMARY OF THE INVENTION

The objects of this invention are provided by a process for separating 3-methyl-2-butanol from 1-butanol which entails the use of certain organic compounds as the agent in extractive distillation.

TABLE 3

Effective Extractive Distillation Agents For Separating 3-Methyl-2-butanol From 1-Butanol

| Compounds | Relative Volatility |
|---|---|
| None | 1.22 |
| Propyl caproate | 1.35 |
| Ethyl n-valerate | 1.8 |
| m-Diethyl benzene | 1.4 |
| Terpinolene | 1.35 |
| 2-Methoxyethanol | 1.4 |
| Dimethylformamide | 1.3 |
| Dimethylacetamide | 1.4 |
| Sulfolane | 1.35 |
| Nitrobenzene | 1.3 |
| Methyl ethyl ketoxime | 1.3 |
| N,N-Dimethylethanolamine | 1.4 |
| Pyridine | 1.3 |
| m-Cresol | 1.35 |
| Phenol | 1.3 |
| 3-Ethyl phenol | 1.35 |
| o-Cresol | 1.3 |
| Dimethylsulfoxide | 1.6* |

*Data Obtained In Multiplate Rectification Column

DETAILED DESCRIPTION OF THE INVENTION

I have discovered that certain organic compounds will greatly improve the relative volatility of 3-methyl-2-butanol to 1-butanol and permit the separation of 3-methyl-2-butanol from 1-butanol by rectification when employed as the agent in extractive distillation. Table 3 lists the compounds that I have found to effective. They are propyl caproate, ethyl n-valerate, m-diethyl benzene, terpinolene, 2-methoxyethanol, dimethylformamide, dimethylacetamide, sulfolane, nitrobenzene, methyl ethyl ketoxime, N,N-dimethylethanolamine, pyridine, m-cresol, phenol, 3-ethyl phenol, o-cresol and dimethylsulfoxide.

THE USEFULNESS OF THE INVENTION

The usefulness or utility of this invention can be demonstrated by referring to the data presented in Tables 1 and 2. All of the successful agents show that 3-methyl-2-butanol can be separated from 1-butanol by means of extractive distillation in a rectification column and that the ease of separation as measured by relative volatility is considerable.

WORKING EXAMPLES

EXAMPLE 1

Thirteen grams of 3-methyl-2-butanol, 27 grams of 1-butanol and 40 grams of ethyl n-valerate were charged to a vapor-liquid equilibrium still and refluxed for five hours. Analysis indicated a vapor composition of 12.4% 3-methyl-2-butanol, 87.6% 1-butanol; a liquid composition of 7.1% 3-methyl-2-butanol, 92.9% 1-butanol. This is a relative volatility of 1.8.

EXAMPLE 2

A solution comprising 80 grams of 3-methyl-2-butanol and 120 grams of 1-butanol was placed in the stillpot of a 5.6 theoretical plate glass perforated plate rectification column. When refluxing began, an extractive agent comprising dimethylsulfoxide was pumped into the top of the column at a rate of 15 ml/min. The temperature of the extractive agent as it entered the column was 83° C. After establishing the feed rate of the extractive agent, the heat input to the 3-methyl-2-butanol - 1-butanol in the stillpot was adjusted to give a total reflux rate of 40 ml/min. After one hour of operation, overhead and bottoms samples were collected and analysed by gas chomatography. The overhead composition was 62.3% 3-methyl-2-butanol, 37.7% 1-butanol and the bottoms composition was 10.6% 3-methyl-2-butanol, 89.4% 1-butanol. This gives a relative volatility of 1.6 for each theoretical plate.

I claim:

1. A method for recovering 3-methyl-2-butanol from a mixture of 3-methyl-2-butanol and 1-butanol which comprises distilling a mixture of 3-methyl-2-butanol and 1-butanol in the presence of from one to five parts by weight of an extractive agent per part of 3-methyl-2-butanol -1-butanol mixture, recovering the 3-methyl-2-butanol as overhead product and obtaining the 1-butanol and the extractive agent as bottoms product, wherein said extractive agent consists of one material selected from the group consisting of propyl caproate, ethyl n-valerate, m-diethyl benzene, terpinolene, 2-methoxyethanol, dimethylformamide, dimethylacetamide, sulfolane, nitrobenzene, methyl ethyl ketoxime, N,N-dimethylethanolamine, pyridine, phenol, o-cresol, m-cresol, 3-ethyl phenol and dimethylsulfoxide.

* * * * *